United States Patent [19]

Tsuruoka et al.

[11] Patent Number: 5,250,545
[45] Date of Patent: Oct. 5, 1993

[54] CANCER CELL METASTASIS INHIBITOR METHODS

[75] Inventors: Tsutomu Tsuruoka; Satoru Nakabayashi; Harumi Fukuyasu; Yuuko Ishii; Takashi Tsuruoka; Haruo Yamamoto; Shigeharu Inouye; Shinichi Kondo, all of Yokohama, Japan

[73] Assignee: Meiji Seika Kaisha, Ltd., Tokyo, Japan

[21] Appl. No.: 621,699

[22] Filed: Dec. 3, 1990

Related U.S. Application Data

[62] Division of Ser. No. 307,387, Feb. 6, 1989, Pat. No. 4,985,445.

[30] Foreign Application Priority Data

| Feb. 12, 1988 | [JP] | Japan | 63-31095 |
| Apr. 15, 1988 | [JP] | Japan | 63-93673 |
| Apr. 19, 1988 | [JP] | Japan | 63-97454 |
| Jun. 14, 1988 | [JP] | Japan | 63-147815 |
| Jun. 14, 1988 | [JP] | Japan | 63-147816 |

[51] Int. Cl.$^5$ .............. C07D 211/06; A61K 31/70
[52] U.S. Cl. ...................... 514/328; 546/219
[58] Field of Search ................... 546/219; 514/328

[56] References Cited

U.S. PATENT DOCUMENTS 4,639,436  1/1987  Junge et al. .................. 514/24

OTHER PUBLICATIONS

Humphries, "Oligosaccharide Modification..." Proc. Natl. Acad. Sci. vol. 83 pp. 1752–1756 Mar. 1986 Cell Biology.

Primary Examiner—Marianne M. Cintins
Assistant Examiner—Catherine S. Kilby Scalzo
Attorney, Agent, or Firm—Jordan and Hamburg

[57] ABSTRACT

Sugar lactams such as N-(3-phenylpropyl)-1-deoxynojirimycin, 1-deoxynojirimycin, D-glucaro-δ-lactam, 6-O-triphenylmethyl-D-gluco-δ-lactam, etc., and new derivatives thereof which inhibit metastasis of cancer cells.

1 Claim, No Drawings

CANCER CELL METASTASIS INHIBITOR METHODS

This is a division of application Ser. No. 07/307,387, filed Feb. 6, 1989 now U.S. Pat. No. 4,985,445.

BACKGROUND OF THE INVENTION

1. Field of the Invention

The present invention relates to compositions capable of markedly inhibiting formation of metastatic lesion of cancer cells and also relates to novel sugar lactams having such an activity.

2. Description of the Prior Art

Main trends in known anticancer agents are drugs to kill malignant cells via cytotoxicity possessed by substances or via human immune system. However, these drugs are yet unsatisfactory for treatment of cancer. To solid cancer, treatment by surgical operation or radiotherapy has been applied and chances of success are greatly improved to the extent that these treatments could eliminate primary cancer. However, the most serious factor for affecting prognosis of the patient with cancer to whom these treatments have been applied is cancer metastasis. Accordingly, it is expected that the effectiveness of the existing various therapies could be further enhanced by inhibiting metastasis of cancer cells. However, there are few substances showing inhibition of metastasis as their main activity and none of them has been used in the clinical field.

SUMMARY OF THE INVENTION

The present invention is based on the finding of substances which can markedly inhibit metastasis of cancer cells and can be used for effective and proper treatment of cancer and aims at providing cancer cell metastasis inhibitors comprising these substances as the effective ingredient.

Metastasis of cancer takes a process of (a) release of cancer cells from primary cancer, (b) seeding into vessel and (c) reaching the target tissue via adherence and extravasation in capillary blood vessel to commence growth.

The present inventors have used the experimental system for evaluation of this cancer metastasis inhibiting activity and have found that compounds represented by general formula (I) described below possess an extremely excellent cancer metastasis inhibiting activity; the present inventors have also prepared compounds represented by general formula (I') as novel compounds exhibiting the activity described above and, thus have accomplished the present invention.

General formula (I)

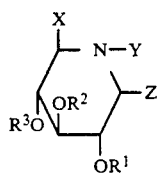

(I)

In formula (I):

a)

X: —CH$_2$OH;
Y: hydrogen atom or

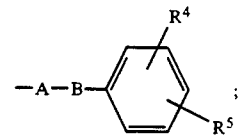

A: hydrocarbon group having 3 to 5 carbon atoms which may or may not contain a double bond;
B: bond or, oxygen atom or sulfur atom;
R$_4$, R$_5$: independently hydrogen atom, halogen atom or a lower alkyl group;
Z: hydrogen atom;
R$^1$, R$^2$, R$^3$: hydrogen atom b)

X: —COOR$^6$ (R$^6$: hydrogen atom or an alkyl group having 1 to 8 carbon atoms, pivaloyloxymethyl group or (5-methyl-2-oxo-1,3-dioxole-4-yl)methyl group);
Y: hydrogen atom;
Z: =O;
R$^1$, R$^2$, R$^3$: hydrogen atom c)

X: —CH$_2$OR$_7$
Y: hydrogen atom;
Z: =O;
R$^1$, R$^2$, R$^7$: independently hydrogen atom or WCO—, wherein W represents an alkyl, a substituted alkyl, an aryl, a substituted aryl, an aralkyl or a substituted aralkyl group (provided that all are not hydrogen atom simultaneously);
R$^3$: hydrogen atom;

or d)

X: —CH$_2$OR$_8$
Y: hydrogen atom;
Z: =O;
R$^1$, R$^3$ independently hydrogen atom or an acyl group;
R$^2$, R$^8$: independently hydrogen atoms,

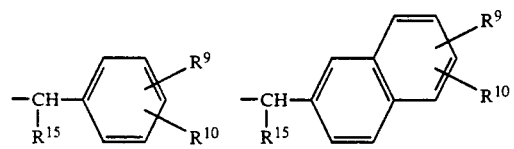

or

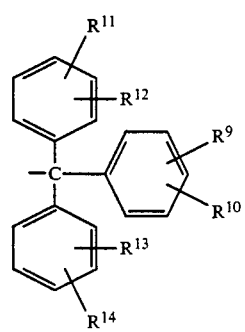

R$^9$-R$^{14}$: independently hydrogen atom, a halogen atom, a lower alkyl, a lower alkoxy, a halogenomethyl, carboxyl, a carboxyalkyl, a carboalkoxyalkyl, phenyl or nitro group $R^{15}$: a lower alkyl group or

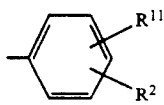

General formula (I')

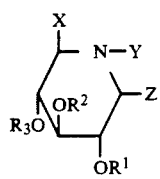
(I')

In formula (I'):
a)
X: —CH$_2$OR$^7$;
Y: hydrogen atom;
Z: =O;
R$^1$, R$^2$, R$^7$: independently hydrogen atom or WCO—, wherein W represents an alkyl, a substituted alkyl, an aryl, a substituted aryl, an aralkyl or a substituted aralkyl group (provided that all are not hydrogen atom simultaneously);
R$^3$: hydrogen atom;
or,
b)
X: —CH$_2$OR$^8$;
Y: hydrogen atom;
Z: =O
R$^1$, R$^3$: hydrogen atom or an acyl group;
R$^2$, R$^8$: independently hydrogen atom,

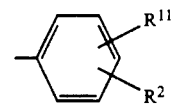

or

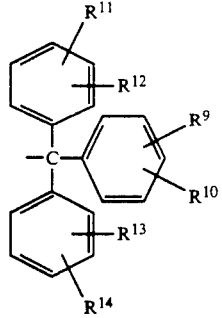

$R^9$-$R^{14}$: independently hydrogen atom, a halogen atom, a lower alkyl, a lower alkoxy, a halogenomethyl, carboxyl, a carboxyalkyl, a carboalkoxyalkyl, phenyl or nitro group
$R^{15}$: a lower alkyl or The compounds represented by general formula (I') of the present invention can be prepared by the following processes.

(1) Production of compounds represented by general formula (I') wherein X, Y, Z, R$^1$, R$^2$ and R$^3$ are described in a) (Compound I'a);

D-Gluco-δ-lactam which is a raw material for synthesis of the compounds can easily be obtained by oxidizing nojirimycin (5-amino-5-deoxy-D-glucopyranose) (Japanese Published Examined Patent Application No. 760/1968, Tetrahedron, 24, 2125-2144, 1968) that is a metabolite of Actinomycetes (Scientific Reports of Meiji Seika Kaisha, No. 13, 80-84, 1973, Japanese Published Examined Patent Application No. 28375/1970).

The sugar lactam derivatives represented by general formula (I'a) of the present invention can be synthesized by the following steps, using this D-gluco-δ-lactam as the raw material.

Process A:

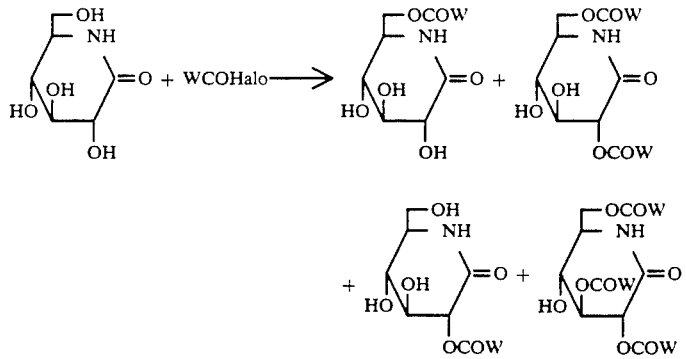

wherein W has the same significance as described above and Halo represents a halogen atom.

The reaction can be performed by first reacting a carboxylic acid component WCOOH (wherein W has the same significance as defined above) with an acid halide synthesis reagent such as thionyl chloride, thionyl bromide, phosphorus oxychloride, etc. in an inert solvent such as methylene chloride, 1, 2-dichloroethane, etc. to give the acid halide (WCOHalo). The reaction is carried out generally at a reaction temperature ranging from 5° to 100° C. and the reaction time is 1 to 24 hours. The thus obtained acid halide is used for the next condensation step, generally without isolating the acid halide, merely by distilling off the reaction solvent under reduced pressure.

The obtained acid halide is dissolved in an inert solvent (N,N-dimethylformamide, halogenated hydrocarbon solvents, acetonitrile, tetrahydrofuran, dioxane, etc.) to form the solution, or, in the absence of any solvent, added to a solution or suspension of D-gluco-δ-lactam in an inert solvent (N,N-dimethylformamide, dioxane, pyridine, halogenated hydrocarbon solvents, etc.) in the presence of an inorganic base such as potassium carbonate, sodium hydrogencarbonate, etc. or an organic base such as triethylamine, pyridine, etc., followed by condensation. The reaction is carried out generally at a reaction temperature ranging from −15° to 80° C.; the reaction time is 1 to 24 hours.

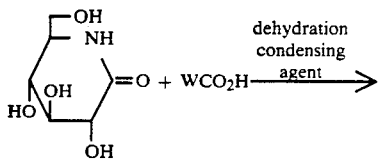

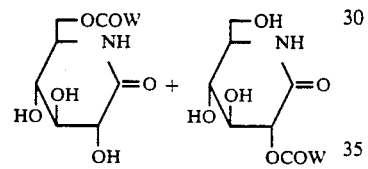

The reaction is carried out by reacting with a carboxylic acid component WCOOH (wherein W has the same significance as described above) and a dehydrating agent, for example, 1, 3-didyclohexylcarbodiimide, diethylcyanophosphate, diphenyl phosphorylazide, p-toluenesulfonyl chloride, triphenylphosphine diethylazodicarboxylate, 1,1'-carbonyldiimidazoler etc,, together, in an inert solvent such as N,N-dimethylformamide, N,N-dimethylacetamide, dimethyl sulfoxide, pyridine, etc., if necessary and desired, in the presence of an organic base such as triethylamine, pyridine, diisopropylethylamine, etc. The reaction is carried out at a reaction temperature generally ranging from 5° to 100° C. and for a reaction time of 1 to 48 hours.

The compound of formula (I'a) thus obtained is collected from the reaction mixture in a conventional manner. The compound (I'a) is isolated, for example, by extraction with an organic solvent or water, precipitation, crystallization or a variety means of chromatography, as a pure substance.

Specific examples of Compound (I'a) include the following compounds: 2-O-(1-(p-chlorobenzoyl)-5-methoxy-2-methylindole-3-acetyl)-D-gluco-δ-lactam, 6-O-(1- (P-chlorobenzoyl) -5-methoxy-2-methyl-indole-3-acetyl)-D-gluco-δ-lactam, 2,6-di-O-(1- (p-chlorobenzoyl) -5-methoxy-2-methyl indole-3-acetyl)-D-gluco-δ-lactam, 2-O-(3-benzoylhydratropoyl)-D-gluco-δ-lactam, 6-O-(3-benzoylhydratropoyl)-D-gluco-δ-lactam, 2, 6-di-O-(3-benzoylhydratropoyl)-D-gluco-δ-lactam, 2-O-(6-methoxy-α-methyl-2-naphthaleneacetyl)-D-gluco-δ-lactam, 6-O-(6-methoxy-α-methyl-2-naphthaleneacetyl)-D-gluco-δ-lactam, 2,6-di-O-(6-methoxy-α-methyl-2-naphthaleneacetyl)-D-gluco-δ-lactam, 6-O-(N-(2,3-xylyl)anthranyloyl)-D-gluco-δ-lactam, 6 -O-(acetylsalicyloyl)-D-gluco-δ-lactam, 2,6-di-O-(acetylsalicyloyl)-D-gluco-δ-lactam, 2,3,6-tri-O-(acetylsalicyloyl)-D-gluco-δ-lactam, 6-O-diphenylacetyl-D-gluco-δ-lactam, 6-O-triphenylacetyl-D-gluco-δ-lactam.

(2) Production of compound shown by general formula (I') wherein X, Y, Z , R¹, R² and R³ are described in b) (Compound I'b): Among Compound I'b, Compound (I-b-A) wherein R² and R⁸ take:

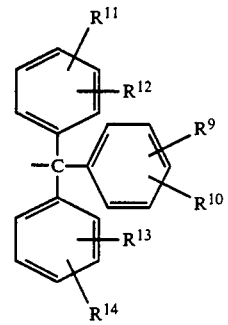

wherein R⁹ through R¹⁴ have the same significance as described above, can be produced by the following reaction scheme:

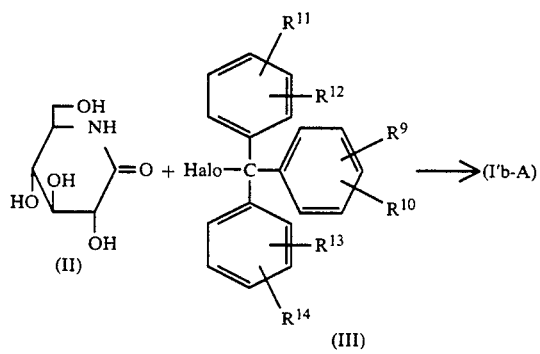

wherein Halo and R⁹ through R¹⁴ have the same significance as described above.

The reacting can be carried out by reaction D-gluco-δ-lactam (II) with activated trityl compound (III) in an inert polar solvent such as N,N-dimethylformamide, N,N-dimethylacetamide, dimethylsulfoxide, pyridine, etc., in the presence of an inorganic base such as potassium carbonate, sodium carbonate, sodium hydride, barium oxide, sodium hydrogencarbonate, etc., or an organic base such as triethylamine, pyridine, diisopropylethylamine, dicyclohexylamine, 1,5-diazabicyclo (4,3,0)non-5-ene, etc., generally at 5° to 100° C. for 1 to 48 hours.

Among Compound I'b, Compound (I'B) wherein R² and R⁸ represent:

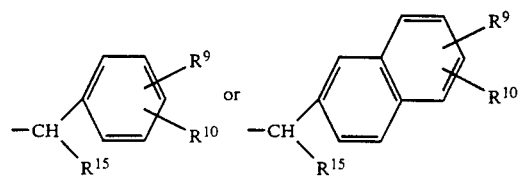

wherein $R^9$, $R^{10}$ and $R^{15}$ have the same significance as described above, can be produced by reacting the following compound:

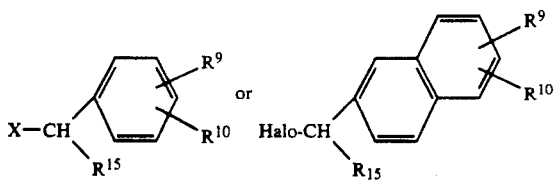

wherein Hal, $R^9$, $R^{10}$ and $R^{15}$ have the same significances as described above, with D-gluco-δ-lactam (II), in a manner similar to the production of Compound (I'b-A) described above.

However, the reaction temperature is generally as high as, for example, 50° to 200° C., or, selectivity to the 3- or 6-position of D-gluco-δ-lactam is low. Therefore, the reaction shown below using diazo compounds is simpler.

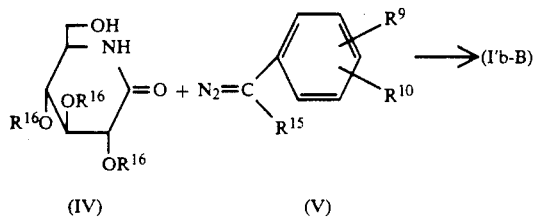

wherein $R^{16}$ represents a hydrogen atom or an acyl protecting group and $R^9$, $R^{10}$ and $R^{15}$ have the same significances as described above.

This reaction is carried out in an inert solvent such as methylene chloride, 1,2-dichloroethane, tetrahydrofuran, dioxane, Acetoner ethyl acetate, toluene, acetonitrile, N,N-dimethylformamide, etc. or a solvent mixture thereof, generally in the presence of an acid catalyst. As the acid catalyst used, mention may be made of protonic acids such as tetrafluoroboric acid, perchloric acid, trifluoromethanesulfonic acid, etc., or tetrafluoroboric acid, tetrachloric tin, ferric chloride, antimony pentafluoride, zinc chloride, etc.

Compound (I'b-B) can be obtained at a reaction temperature of from −60° to +500° C. for a reaction time of 1 to 24 hours.

Specific examples of Compound I'b include the following compounds:

3-O-trityl-D-gluco-B-lactam, 6-O-trityl-D-gluco-δ-lactam, 3, 6-di-O-trityl-D-gluco-δ-lactam, 6-O-(3, 5-ditrifluoromethyl-trityl)-D-gluco-δ-lactam, 6-O-(3,3'-butyltrityl)-D-gluco-δ-lactam, 6-O-(4-tert-butyltrityl)-D-gluco-δ-lactam, 6-O-(4-carboxytrityl)-D-gluco-δ-lactam, 6-O-benzhydryl-D-gluco-δ-lactam, 6-O-(3,3'-ditrifluoromethylbenzhydryl)-D-gluco-δ-lactam, 6-O-(1-β-naphthylethyl)-D-gluco-δ-lactam, 6-O-(p-phenylbenzhydryl)-D-gluco-δ-lactam, 6-O-(1-phenylethyl)-D-gluco-δ-lactam, 6-O-(2-chloro-5-nitrobenzhydryl)-D-gluco-δ-lactam, 6-O-(3,4-dichlorobenzhydryl)-D-gluco-δ-lactam, 6-O-(4,4'-dichlorobenzhydryl)-D-gluco-δ-lactam, 6-O-(2,4-difluorobenzhydryl)-D-gluco-δ-lactam, 6-O-(4-nitrobenzhydryl)-D-gluco-δ-lactam, 6-O-(1-p-phenoxyethyl)-D-gluco-δ-lactam, 6-O-(3,4-dimethylbenzhydryl)-D-gluco-δ-lactam, 6-O-(m-(1-tert-butyloxycarbonylethyl)benzhydryl)-D-gluco-δ-lactam.

(3) Production of compound shown by general formula (I) wherein X, Y, Z, $R^1$, $R^2$ and $R^3$ are described in a) (Compound Ia).:

1-Deoxynojirimycin which is a raw material of Compound Ia is a known compound obtained by reduction of nojirimycin (Tetrahedron, 24, 2125 (1968)). Further N-substituted-1-deoxynojirimycins can be obtained by reacting 1-deoxynojirimycin as a raw material with an alkyl halide in a polar solvent such as dimethylformamide (DMF) in the presence of a base such as sodium hydrogencarbonate and isolating the product from the reaction solution (cf. Japanese Published Unexamined Patent Application Nos. 9051/1980 and 47655/1980).

Specific examples of Compound Ia include the following compounds:

N-(3-phenylpropyl)-1-deoxynojirimycin, N-(4-phenylbutyl)-1-deoxynojirimycin, N-(3-phenylbutyl)-1-deoxynojirimycin, N-(5-phenylpentyl)-1-deoxynojirimycin, N-(3-phenyl-2-propenyl)-1-deoxynojirimycin, N-(4-phenyl-3-butenyl)-1-deoxynojirimycin, N-(3-methyl-3-phenyl-2-propenyl)-1-deoxynojirimycin, N-(3-m-methylphenyl-2-propenyl)-1-deoxynojirimycin, N-(3-p-methylphenyl-2-propenyl)-1-deoxynojirimycin, N-(3-o-chlorophenyl-2-propenyl)-1-deoxynojirimycin, N-(3-p-chlorophenyl-3-methyl-2-propenyl)-1-deoxynojirimycin, N-(3-p-methylphenyl-3-methyl-2-propenyl)-1-deoxynojirimycin, N-(3-p-bromophenyl-2-propenyl)-1-deoxynojirimycin, N-(2-phenoxyethyl)-1-deoxynojirimycin, N-(3-phenoxypropyl)-1-deoxynojirimycin, N-(3-thiophenoxypropyl)-1-deoxynojirimycin, N-(4-phenoxybutyl)-1-deoxynojirimycin, N-(5-phenoxypentyl)-1-deoxynojirimycin, N-(3-phenoxy-trans-propen-1-yl)-1-deoxynojirimycin, N-(3-phenoxy-trans-2-propenyl)-1-deoxynojirimycin, N-(4-phenoxy-trans-2-butenyl)-1-deoxynojirimycin, N-(4-thiophenoxy-trans-2-butenyl)-1-deoxynojirimycin, N-(3-m-methylphenoxypropyl)-1-deoxynojirimycin, N-(3-o-methylphenoxypropyl)-1-deoxynojirimycin, N-(3-p-methylphenoxypropyl)-1-deoxynojirimycin, N-(3-p-chloro-phenoxy-3-methyl-2-propenyl)-1-deoxynojirimycin, N-(3-p-methyl-phenoxy-3-methyl-2-propenyl)-1-deoxynojirimycin, N-(3-p-chloro-phenoxy-2-propenyl)-1-deoxynojirimycin, N-(3-m-fluorophenoxy-2-propenyl)-1-deoxynojirimycin, N-(3-p-bromophenoxy-2-propenyl)-1-deoxynojirimycin, N-(4-p-chlorophenoxy-trans-2-butenyl)-1-deoxynojirimycin.

(4) Production of compound shown by general formula (I) wherein X, Y, Z, $R^1$, $R^2$ and $R^3$ are described in b) (Compound Ib);

Among Compound Ib, the method of producing D-glucaro-δ-lactam has been achieved through chemical or enzymatical oxidation of nojirimycin by the present inventors. That is, nojirimycin is subjected to chemical oxidation or to treatment with glucose oxidase to give the oxidation product of the hydroxy group at the 1-position thereof (D-gluco-δ-lactam), which is then subjected to catalytic oxidation with air to give D-glucaro-δ-lactam (cf. Scientific Reports of Meiji Seika Kaisha, No. 13, 80–84, 1973 and Japanese Published Examined Patent Application No. 28375/1970).

D-Glucaro-δ-lactam alkyl esters can be obtained by reacting D-glucaro-δ-lactam with an alkyl halide or a diazoalkane in methanol, tetrahydrofuran, dioxane, N,N-dimethylformamide, etc. or a solvent mixture thereof (cf. Japanese Published Examined Patent Application Nos. 34589/1981 and 34590/1981).

Specific examples of Compound Ib include the following compounds.

D-glucaro-δ-lactam, D-glucaro-δ-lactam methyl ester, D-glucaro-δ-lactam ethyl ester, D-glucaro-δ-lactam propyl ester, D-glucaro-δ-lactam-n-butyl ester, pivaloyloxymethyl ester, 5-methyl-2-oxo-1,3-dioxole-4-yl methyl ester.

Further examples of pharmacologically acceptable salts of the compounds of the present invention include ammonium salts; salts of alkali metals such as sodium, potassium, etc.; salts of alkaline earth metals such as magnesium, calcium, etc.; salts with organic base such as triethylaminer triethanolamine, diethylaminoethylamine, etc.; salts with heterocyclic amines such as piperidine, piperazine, morpholine, etc.; or salts with amino acids such as lysine, etc.

Some of these compounds are known to have therapeutic effects for diabetes, (Japanese Published unexamined Patent Application Nos. 9051/1980, 47655/1980 and 166616/1985). Furthermore, it has been made clear by the present inventors that the compounds falling under general formulae Ia, Ib and Id among the compounds of the present invention are also effective as therapeutic agents for human immunodeficiency virus (HIV) diseases (Japanese Patent Application Nos. 171376/1988, 328387/1987 and 326747/1987).

The cancer cell metastasis inhibitor of the present invention is administered clinically as oral or parenteral preparations via vein, artery, skin, hypoderm, rectum and muscle or orally. Further by administering against tumor more potent effects can be expected. Dose may vary depending upon mode of application, preparatory form or age, body weight and condition of patient but generally a dose of 100 to 3000 mg is given once a day or in several portions a day.

As parenteral preparations, mention may be made of sterile aqueous or non-aqueous solution or an emulsion. As bases for the non-aqueous solution or emulsion, mention may be made of propylene glycol, polyethylene glycol, glycerin, olive oil, corn oil, ethyl olerate, etc. As oral preparations, mention may be made of capsules, tablets, granules, granulates, powders, etc. In these preparations, starch, lactose, mannitol, ethyl cellulose, sodium carboxymethyl cellulose, etc. are formulated as excipients, and as lubricants, magnesium stearate or calcium stearate is added to the preparations. As binders, gelatin, gum arabic, cellulose esters, polyvinyl pyrrolidone, etc. can be used.

Some examples of the acute toxicities toxities ($LD_{50}s$) mice in the claimed compounds are shown in Table 1.

TABLE 1

| Compound | LD$_{50}$ Value Administration Route | LD$_{50}$ |
| --- | --- | --- |
| N-(3-phenylpropyl)-1-deoxynojirimycin | i.p. | >0.5 g/kg |
| N-(3-phenyl-2-propenyl)-1-deoxynojirimycin | i.p. | >0.5 g/kg |
| N-(4-phenoxy-trans-2-butenyl)-deoxynojirimycin | i.p. | >0.5 g/kg |
| D-Glucaro-δ-lactam sodium salt | i.v. | >3 g/kg |
| D-Glucaro-δ-lactam sodium salt | p.o. | >5 g/kg |
| D-Glucaro-δ-lactam methyl ester | i.v. | >5 g/kg |
| D-Glucaro-δ-lactam methyl ester | p.o. | >10 g/kg |
| 2,6-Di-O-(acetylsalicyloyl)-D-gluco-δ-lactam | i.p. | >0.5 g/kg |
| 6-O-Triphenylmethyl-D-gluco-δ-lactam | s.c. | >0.3 g/kg |

TABLE 1-continued

| Compound | LD$_{50}$ Value Administration Route | LD$_{50}$ |
| --- | --- | --- |
| δ-lactam | | |

Formulation examples of the present invention are described below.

FORMULATION EXAMPLE 1

| N-(3-p-Bromophenyl-2-propenyl)-1-deoxynojirimycin | 50 mg |
| --- | --- |
| Lactose | 130 mg |
| Potato starch | 70 mg |
| Polyvinylpyrrolidone | 10 mg |
| Magnesium stearate | 2.5 mg |

Lactose and potato starch are mixed and 20% ethanol solution of polyvinylpyrrolidone is added to the mixture. After uniformly wetting, the mixture is passed through a sieve of 1 mm, dried at 450° C. and again passed through a sieve of 1 mm. The thus obtained granules are kneaded with magnesium stearate and the mixture is prepared into tablets.

FORMULATION EXAMPLE 2

N-(5-Phenylpentyl)-1-deoxynojirimycin is ground until it becomes particles of about 10 microns. Then, 500 mg of the particles is filled in a bial for injection. Separately, 5 mg of Tween 80 and 10 mg of purified gelatin according to the Japanese Pharmacopeia are dissolved in 5 ml of distilled water for injection to make a dissolution liquid. Upon use, 5 ml of this dissolution solution is added to N-(5-phenylpentyl)-1-deoxynojirimycin filled in the bial. The mixture is thoroughly shaken to make a suspension and a suitable dose of the suspension is intramuscularly administered.

FORMULATION EXAMPLE 3

| N-(3-Phenoxypropyl)-1-deoxynojirimycin | 50 mg |
| --- | --- |
| Lactose | 130 mg |
| Potato starch | 70 mg |
| Polyvinylpyrrolidone | 10 mg |
| Magnesium stearate | 2.5 mg |

N-(3-Phenoxypropyl)-1-deoxynojirimycin, lactose and potato starch are mixed and 20% ethanolic solution of polyvinylpyrrolidone is added to the mixture to uniformly wet the mixture. The wet mixture is passed through a sieve of 1 mm, dried at 450° C. and again passed through a sieve of 1 mm. The thus obtained granules are kneaded with magnesium stearate to form into tablets.

FORMULATION EXAMPLE 4

After grinding N-(3-m-methylphenoxypropyl)-1-deoxynojirimycin with a pin mill to particles of about 10 microns, 500 mg of the particles are filled up in a bial for injection. Separately, 5 mg of Tween 80 and 10 mg of gelatin purified according to the Japanese Pharmacopeia are dissolved in 5 ml of distilled water for injection to make a dissolving liquid. Upon use, 5 ml of this dissolving liquid is added to N-(3-m-methylphenoxypropyl)-1-deoxynojirimycin filled in the bial described above and the mixture is thoroughly shaken to make a suspension. A suitable dose of the suspension is intramuscularly administered.

FORMULATION EXAMPLE 5

| D-Glucaro-δ-lactam potassium salt | 50 mg |
| --- | --- |
| Lactose | 130 mg |
| Potato starch | 70 mg |
| Polyvinylpyrrolidone | 10 mg |
| Magnesium stearate | 2.5 mg |

D-Glucaro-δ-lactam potassium salt, lactose and potato starch are mixed and 20% ethanolic solution of polyvinylpyrrolidone is added to the mixture to uniformly wet the mixture. The mixture is passed through a sieve of 1 mm, dried at 450° C. and again passed through a sieve of 1 mm. The thus obtained granules are kneaded with magnesium stearate to form into tablets.

FORMULATION EXAMPLE 6

| D-Glucaro-δ-lactam ethyl ester | 200 mg |
| --- | --- |
| Lactose | 50 mg |
| CMC calcium | 100 mg |
| Magnesium stearate | 3 mg |

The foregoing composition was filled in hard gelatin capsules to prepare capsules.

FORMULATION EXAMPLE 7

D-Glucaro-δ-lactam sodium salt was dissolved in distilled water for injection in a concentration of 50 mg/ml and 5 ml each per 1 ampoule was aseptically poured into each ampoule and the ampoule was sealed.

FORMULATION EXAMPLE 8

| 6-O-[1-(p-Chlorobenzoyl)-5 methoxy-2-methylindole-3-acetyl]-D-Gluco-δ-lactam | 50 mg |
| --- | --- |
| Lactose | 130 mg |
| Potato starch | 70 mg |
| Polyvinylpyrrolidone | 10 mg |
| Magnesium stearate | 2.5 mg |

Lactose and potato starch were mixed and 20% ethanolic solution of polyvinylpyrrolidone was added to the mixture to uniformly wet the mixture. The mixture was passed through a sieve with a mesh of 1 mm, dried at 450° C. and again passed through a sieve with a mesh of 1 mm. The thus obtained granules were mixed with magnesium stearate to form into tablets.

FORMULATION EXAMPLE 9

After grinding 6-O-[N-(2,3-xylyl)anthranyloyl]-D-gluco-δ-lactam with a pin mill to particles of about 10 microns, 500 mg of the particles were filled in a bial for injection. Separately, 5 mg of Tween 80 and 10 mg of gelatin purified according to the Japanese Pharmacopeia were dissolved in 5 ml of distilled water for injection to make a dissolving liquid. Upon use, 5 ml of this dissolving solution was added to 6-O-[N-(2,3-xylyl)anthranyloyl]-D-gluco-δ-lactam. The mixture was thoroughly shaken to form a suspension and a suitable dose of the suspension was intramuscularly administered.

FORMULATION EXAMPLE 10

| 6-O-Triphenylmethyl-D-gluco-δ-lactam | 200 mg |
| --- | --- |
| Lactose | 130 mg |
| Potato starch | 70 mg |
| Polyvinylpyrrolidone | 10 mg |
| Magnesium stearate | 2.5 mg |

Lactose and potato starch were mixed and 20% ethanolic solution of polyvinylpyrrolidone was added to the mixture to uniformly wet the mixture. The mixture was passed through a sieve with a mesh of 1 mm, dried at 45° C. and again passed through a sieve with a mesh of 1 mm. The thus obtained granules were mixed with magnesium stearate to form into tablets.

FORMULATION EXAMPLE 11

After grinding 6-O-(3,3'-ditrifluoromethyltrityl)-D-gluco-δ-lactam with a pin mill to particles of about 10 microns, 500 mg of the particles were filled in a bial for injection.

In the case of administering this injection, a dissolving liquid obtained by dissolving 5 mg of TWEEN 80 and 10 mg of gelatin purified according to the Japanese Pharmacopeia in 5 ml of distilled water was mixed with the above-mentioned particles and the mixture was well shaken to form a suspension. A suitable dose of the suspension was intramuscularly administered.

Hereafter preparation examples of the novel compounds of the present invention are shown below.

PREPARATION EXAMPLE 1

6-O-(6-Methoxy-α-methyl-2-naphthaleneacetyl)-D-gluco-δ-lactam:

D-Gluco-δ-lactam, 5.31 g (30 mmols), and 6.9 g (30 mmols) of 6-methoxy-a-methyl-27naphthalene acetic acid were dissolved in 50 ml of DMF and 7 ml of triethylamine and 6.7 ml of diethyl cyanophosphonate were added to the solution. The mixture was stirred at room temperature overnight. After filtering off insoluble matters, the filtrate was concentrated to give 5 g of the residue. The residue was dissolved in ethyl acetate and water. The ethyl acetate phase was separated and concentrated to give 3.8 g of oil. The oil was separated by silica gel chromatography (chloform:methanol=10:1) to give 1.6 g of the title compound (silica gel thin layer chromatography (chloroform:methanol=4:1), Rf=0.46).

PREPARATION EXAMPLE 2

2-O- (6-Methoxy-α-methyl-2-naphthaleneacetyl)-D-gluco-δ-lactam and 2,6-di-O-(6-Methoxy-α-methyl-2-naphthaleneacetyl)-D-gluco-δ-lactam:

6-Methoxy-α-methyl-2-naphthaleneacetic acid, 11.5 g was dissolved in 160 ml of methylene chloride and 0.1 ml of dimethylformamide and 7.3 ml of thionyl chloride was added to the solution. The mixture was stirred at room temperature for 5 hours. After the solvent was distilled off, toluene was added thereto and the mixture was further concentrated to dryness to give the acid chloride.

D-Gluco-δ-lactam, 5.85 g, was dissolved in 100 ml of dimethylformamide and 12 ml of pyridine was added to the solution. The mixture was cooled to 5° C. and the acid chloride of 6-methoxy-α-methyl-2-napthaleneacetic acid was added to the mixture. The resulting mixture was stirred at room temperature overnight. After filtering off insoluble matters, the solvent was distilled off and toluene was further added to the residue. The mixture was further concentrated to dryness to give the residue. Ethyl acetate and water were added to the residue. Firstly insoluble matters were taken by filtration and 1.8 g of 2-O-(6- methoxy-α-methyl-2-naphthaleneacetyl)-D-gluco-δ-lactam(silica gel thin layer chromatography (chloroform:methanol = 10:1), Rf = 0.26) was obtained.

Then, the ethyl acetate phase was separated and concentrated to make the amount of ethyl acetate 150 ml. Insoluble matters were taken by filtration and 5.86 g of 2, 6-di-O-(6-methoxy-a-methyl-2-naphthaleneacetyl)-D-gluco-δ-lactam(silica gel thin layer chromatography (chloroform:methanol = 10:1), Rf = 0.48) was obtained.

PREPARATION EXAMPLE 3

6-O-(1-(p-Chlorobenzoyl)-5-methoxy-2-methyl-3-indoleacetyl)-D-gluco-α-lactam and 2, 6-di-O-(1-(p-chlorobenzoyl) -5-methoxy-2-methyl-3-indoleacetyl)-D-gluco-δ-lactam;

Indomethacin, 5.37 g, was dissolved in 50 ml of 1,2-dichloroethane and 0.1 ml of dimethylformamide and 2.25 ml of thionyl chloride was added to the solution. The mixture was stirred at 60° C. for 1.5 hours. After concentration, toluene was added and the mixture was further concentrated to give the acid chloride of Indomethacin.

D-Gluco-δ-lactam, 2 g, was dissolved in a mixture of 50 ml of dimethylformamide and 1.7 ml of pyridine and the solution was cooled to 50° C. Then, a solution of the acid chloride of Indomethacin in 20 ml of dimethylformamide was added to the solution and the mixture was stirred at room temperature overnight. The solvent was distilled off and separation was made directly by means of silica gel column chromatography (chloroform:methanol = 20:1) to give 0.7 g of 6-O-(1-(p-chlorobenzoyl)-5-methoxy-2-methyl-3-indoleacetyl)-D-gluco-δ-lactam and 0.7 g of 2-O-(1-(p-chlorobenzoyl)-5-methoxy-2-methyl-3-indoleacetyl)-D-gluco-δ-lactam (silica gel thin layer chromatography (chloroform:methanol = 10:1), Rf = 0.33) as well as 2.16 g of 2,6-di-O-(1-(p-chlorobenzoyl)-5-methoxy-2-methyl-3-indoleacetyl)-D-gluco-δ-lactam (silica gel thin layer chromatography (chloroform:methanol = 10:1), Rf = 0.56).

PREPARATION EXAMPLE 4

2,6-Di-O-(3-benzoylhydratropoyl)-D-gluco-δ-lactam;

Ketoprofen, 5.08 g, was dissolved in a mixture of 50 ml of 1,2-dichloroethane and 0.1 ml of dimethylformamide and 2.95 ml of thionyl chloride was added to the solution. The mixture was stirred at 600° C. for 2 hours. The solvent was distilled off and toluene was added to the residue. Toluene was further distilled off to give the acid chloride of Ketoprofen.

D-Gluco-δ-lactam, 3.54 g, was dissolved in 35 ml of dimethylformamide and 4 ml of pyridine. The solution was cooled to 5° C. A solution of the acid chloride of Ketoprofen in 20 ml of dimethylformamide was added to the solution. The solvent was distilled off and 40 ml of water, 40 ml of methanol and 150 ml of ethyl ether were added to the residue to make a dual layer solution. Thereafter the ethereal phase was separated. After the ethereal phase was further washed with a sodium bicarbonate aqueous solution, the solution was distilled off and then separation was performed by means of silica gel column chromatography (chloroform:methanol = 40:1) to give 1.98 g of the title compound (silica gel thin layer chromatography (chloroform:methanol = 10:1), Rf = 0.44).

PREPARATION EXAMPLE 5

6-O-(N- (2, 3-Xylyl) anthranyloyl)-D-gluco-δ-lactam:

D-Gluco-δ-lactam, 5.31 g, and 7.23 g of mefenamic acid were dissolved in 60 ml of dimethylforamide and, 6.3 ml of triethylamine and then 6.6 ml of diethyl cyanophosphonate were added to the solution. The mixture was stirred at room temperature overnight. After distilling the solvent off, ethyl ether was added to the residue and the mixture was stirred at room temperature. Thereafter insoluble matters were taken by filtration. A small quantity of methanol was added to the filtered solid to make a solution. Then, ethyl ether and isopropyl ether were added to the solution. The precipitates were taken by filtration. The obtained precipitates were further dissolved in methanol to make a solution. Isopropyl ether was added to the solution to again make a methanolic solution. Isopropyl ether was added to again cause precipitation and give 1.42 g of the title compound (silica gel thin layer chromatography (chloroform:methanol = 4:1), Rf = 0.51).

(PREPARATION EXAMPLE 6)

6-O-(Acetylsalicyloyl)-D-gluco-δ-lactam, 2,6-di-O-(acetylsalicyloyl)-δ-gluco-8-lactam and 2,3,6-tri-O-(acetylsalicyloyl)-δ-gluco-8-lactam:

D-Gluco-δ-lactam, 3.52 g, was suspended in a mixture of 50 ml of pyridine and 15 ml of N,N-dimethylformamide. Under ice cooling, a solution of 8.0 g of O-acetylsalicyloyl chloride in 50 ml of N,N-dimethylformamide was dropwise added to the suspension. After stirring at 0° to 50° C. for an hour, the temperature was reverted to room temperature. After reacting overnight while stirring,, insoluble matters were filtered off and the filtrate was concentrated to dryness. The residue was purified by silica gel column chromatography (chloroform:methanol = 10:1) to give 0.3 g of 6-0-(acetylsalicyloyl)-D-gluco-δ-lactam (silica gel thin layer chromatography (chloroform:methanol = 10:1), Rf = 0.11), 3.0 g of 2,6-di-0-(acetylsalicyloyl)-D-gluco-δ-lactam (silica gel thin layer chromatography (chloroform:methanol = 10:1), Rf = 0.41) and 0.4 g of 2,3,6-tri-O- (acetylsalicyloyl)-D-gluco-δ-lactam (silica gel thin layer chromatography (chloroform:methanol = 10:1) , Rf = 0.53), respectively.

(PREPARATION EXAMPLE 7

6-O-(3,5-Ditrifluoromethylbenzhydryl)-D-gluco-δ-lactam:

The hydrazon compound, 1.0 g, synthesized from 3,5-ditrifluoro-methylbenzophenone in a conventional manner was dissolved in 20 ml of ethyl acetate and 3.0 g of nickel peroxide was added to the solutions The mixture was stirred at room temperature for an hour.

After removing insoluble matters, ethyl acetate was distilled off below 30° C. to give 0.95 g of the diazo compound.

The obtained diazo compound, 0.95 g, and 500 mg of 2,3,4-tri-O-acetyl-D-gluco-8-lactam were dissolved in 10 ml of 1,2-dichloroethane. The solution was cooled to 5° C. While stirring, a solution of 40 mg of trifluoroboric acid etherate in 1 ml of 1,2-dichloroethane was dropwise added to the solution slowly in argon flow. After completion of the dropwise addition, the mixture was stirred at 5° C. for 30 minutes and then concentrated.

The thus obtained liquid was purified by silica gel column chromatography (toluene : ethyl acetate=2:1) to give 540 mg of 2,3,4-tri-O-acetyl-6-O-(3,5-ditrifluoromethylbenzhydryl)-D-gluco-δ-lactam(silica gel thin layer chromatography (toluene:ethyl acetate=1:1), Rf=0.34).

The thus obtained 2,3,4-tri-O-acetyl 6-O-substituted compound, 270 mg, was dissolved in 4 ml of methanol and a methanolic solution of sodium methoxide freshly prepared was added to the solution at any time followed by stirring at room temperature.

The reaction was monitored by silica gel thin layer chromatography (chloroform:methanol=4:1). After completion of the reaction, the same amount of water as that of the reaction solution was added to the reaction solution. Thereafter, the mixture was treated with Amberlist 15 to remove sodium ions and then concentrated to dryness. To the residue was added 5 ml of diethyl ether. The mixture was stirred at room temperature for 30 minutes. Insoluble solid was taken by filtration to give 150 mg of the title compound(silica gel thin layer chromatography (chloroform:methanol=4:1), Rf=0.61; mass spectrum (F.D. mass) m/z: 479 (M+)).

PREPARATION EXAMPLE 8

6-O-(3,3'-Ditrifluoromethylbenzhydryl)-D-gluco-δ-lactam:

Using the hydrazone compound for 3,3'-ditrifluoromethyl-benzhydrylation instead of the hydrazone compound for 3,5-ditrifluoromethylbenzhydrylation in Preparation Example 7, the title compound (silica gel thin layer chromatography (chloroform:methanol=4:1), Rf=0.51; mass spectrum (F.D. mass) m/z:480 (M+) was obtained in a manner similar to Preparation Example 7.

PREPARATION EXAMPLE 9

6-O-p-Phenylbenzyhydryl-D-gluco-δ-lactam:

Using the hydrazone compound for P-phenylbenzhydrylation instead of the hydrazone compound for 3,5-ditrifluromethylbenzhydrylation in Preparation Example 7, the title compound (silica gel thin layer chromatography (chloroform:methanol=4:1), Rf=0.64; mass spectrum (F.D. mass) m/z:419 (M+)) was obtained in a manner similar to Preparation Example 7.

PREPARATION EXAMPLE 10

6-O-(1-β-Naphthylethyl)-D-gluco-δ-lactam:

Using the hydrazone compound for 1-β-naphthylethylation instead of the hydrazone compound for 3,5-ditrifluoromethylbenzhydrylation in Preparation Example 7, the title compound (silica gel thin layer chromatography (chloroform methanol=4:1), Rf=0.4; mass spectrum (F.D. mass) m/z:331 (M+)) was obtained in a manner similar to Preparation Example 7.

PREPARATION EXAMPLE 11

6-O-(1-(3,4-Dimethoxyphenyl) ethyl) -D-gluco-δ-lactam:

Using the hydrazone compound for (3,4-dimethoxyphenyl)ethylation instead of the hydrazone compound for 3,5-ditrifluoromethylbenzhydrylation in Preparation Example 7, the title compound (silica gel thin layer chromatography (chloroform:methanol=4:1), Rf=0.43; mass spectrum (F.D. mass) m/z:341 (M+))was obtained in a manner similar to Preparation Example 7.

PREPARATION EXAMPLE 12

6-O-(3,4-Dichlorobenzhydryl)-D-gluco-δ-lactam:

Using the hydrazone compound for 3,4-dichlorobenzhydrylation instead of the hydrazone compound for 3,5-ditrifluoromethylbenzhydrylation in Preparation Example 7, the title compound (silica gel thin layer chromatography (chloroform:methanol=4:1), Rf=0.46; mass spectrum (F.D. mass) m/z:411 (M+)) was obtained in a manner similar to Preparation Example 7.

PREPARATION EXAMPLE 13

3,6-Di-O-trityl-D-gluco-δ-lactam:

D-Gluco-δ-lactam, 1.7 9, and 5.6 9 of trityl chloride were mixed with 50 ml of pyridine. The mixture was stirred overnight with heating at 50°C. After pyridine was distilled off,,,chloroform and saturated aqueous sodium bicarbonate solution were added to the residue followed by extraction with chloroform 3 times. After drying the chloroform phase over anhydrous potassium carbonate, chloroform was distilled off and the residue was purified by.-silica gel thin layer chromatography (chloroform:methanol=70:1) to give 0.8 g of the title compound. (silica gel thin layer chromatography (chloroform:methanol=50:1), Rf=0.25; mass spectrum (F.D. mass) m/z:660 (M+)).

PREPARATION EXAMPLE 14

6-O-(3,3'-Ditrifluoromethyltrityl)-D-gluco-δ-lactam:

D-Gluco-δ-lactam, 1.06 g, and 3.0 g of 3,3'-ditrifluoromethyltrityl chloride were dissolved in 40 ml of pyridine. The mixture was heated at 60° C. overnight while stirring. After pyridine was distilled off, ethyl acetate and saturated sodium bicarbonate aqueous solution were added to the residue. After the aqueous phase was further saturated with sodium chloride, the system was extracted with ethyl acetate 3 times. After drying the ethyl acetate phase over anhydrous potassium carbonate, the solvent was distilled off and the residue was purified by silica gel column chromatography (chloroform:methanol=20:1) to give 600 mg of the title compound (silica gel thin layer chromatography (chloroform:methanol=10:1), Rf=0.23).

PREPARATION EXAMPLE 15

6-δ-(3,5-Ditrifluoromethyltrityl)-D-gluco-δ-lactam:

Using 3,5-ditrifluoromethyltrityl chloride instead of 3,3'-ditrifluoromethyltrityl chloride in Preparation Example 14, the title compound (silica gel thin layer chromatography (chloroform:methanol=4:1), Rf= 0.53, mass spectrum (F.D. mass) m/z:555 (M+)) was obtained in a manner similar to Preparation Example 14.

PREPARATION EXAMPLE 16

6-O-(4-tert-butyltrityl)-D-gluco-δ-lactam:

Using 4-tert-butyltrityl chloride instead of 3,3'-ditrifluoromethyltrityl chloride in Preparation Example 14, the title compound (silica gel thin layer chromatography (chloroform-methanol=6:1), Rf=0.38; mass spectrum (F.D. mass) m/z:475 (M+)) was obtained in a manner similar to Preparation Example 14.

The effectiveness of the, compounds according to the present invention was determined by the following method.

TEST METHODS

Based on the method described priviously (Method in Cancer Research, 15, 399–439, 1978), a subline of high metastatic potential (high pulmonary colonization) was selected from murine melanoma B16 by repeating the i.v. transplantation of the tumor cells in BDF, mice and the isolation of pulmonary metastatic clones.

Evaluation of the metastasis inhibiting activity was performed based on the method described previously (Proc. Natl Acad. Sci. USA, 83, 1752–1756, 1986, Cancer Research, 46, 858–862, 1986).

Firstly, the B16 subline of high metastatic potential was inoculated into Dulbeccol's ME medium (DME medium) supplemented with 10 % bovine fetal serum and the compound represented by general formula (I) described above was added thereto. Incubation was performed at 37° C. for 2 to 4 days in the presence of 5% $CO_2$ and proliferated cells were detached from the Petri dish with trypsin-EDTA solution. The cells were suspended in divalent cation-free Dulbecco's phosphate-buffered saline (PBS-) in $1\times10^6$ cells/ml as viable cells.

This suspension, 0.1 ml, was intravenously injected in the mouse tail vein. After feeding for 14 days, the mouse was sacrificed to excise the lungs. The number of metastatic nodules of the B16 subline of high pulmonary metastatic potential on the surface of and in the lungs was counted.

TEST EXAMPLE 1

Cytotoxic activity of N-(3-phenylpropyl)-1-deoxynojirimycin:

The B16 subline of high pulmonary metastatic potential and murine tumor cell line L 929 were cultured in DME medium supplemented with 10% bovine fetal serum at 37° C. in the presence of 5% $CO_2$. Then, cells were detached from the Petri dish with trypsin-EDTA solution. The B16 subline and L 929 were suspended in the medium described above in $1\times10^4$ cells/ml and $1\times10^3$ cells/ml, respectively. Each suspension, 150 μl, was added to 50 μl of N-(3-phenylpropyl)-1-deoxynojirimycin solution or Adriamycin (control) solution. Incubation was performed for 3 days for the B16 subline and for 4 days for L 929 strain. Cell growth was observed with the aid of an inverted microscope to determine the cytotoxicity. The results are shown in Table 2.

TABLE 2

| Drug Added | Concentration | Growth |
|---|---|---|
| Cell Line: B16 Subline of High Pulmonary Metastatic Potential | | |
| None | | + |
| N-(3-Phenylpropyl)- | 30 μg/ml | + |
| 1-deoxynojirimycin | | |
| | 100 μg/ml | + |
| | 300 μg/ml | ± |
| Adriamycin (control) | 0.1 μg/ml | − |
| Cell Line: L 929 | | |
| None | | + |
| N-(3-Phenylpropyl)- | 0.5 μg/ml | + |
| 1-deoxynojirimycin | | |
| | 5 μg/ml | + |
| | 50 μg/ml | + |
| | 100 μg/ml | + |
| Adriamycin (control) | 1 μg/ml | − |

In the table:
+ indicates growth;
± indicates growth in which marked inhibition is noted.
− indicates death As shown in Table 2, N-(3-phenylpropyl)-1-deoxynojirimycin which is the effective ingredient of the present invention did not show marked cytotoxicity against the B16 subline of high pulmonary metastatic potential and L 929 even at a concentration as high as 100 μg/ml.

TEST EXAMPLE 2

Inhibition of metastasis by N-(3-phenylpropyl)-1-deoxynojirimycin:

The B16 subline of high pulmonary metastatic potential was inoculated into DME medium supplemented with 10% um and 30, 100 or 300 μg/ml of N-(3-phenylpropyl)-1-deoxynojirimycin was added thereto followed by incubation at 37° C. for 3 days in the presence of 5% $CO_2$. The cells were detached from the Petri dish with trypsin-EDTA solution. The cells were suspended in PBS- in $1\times10^6$ cells/ml as viable cells. This suspension, 0.1 ml, was intravenously injected in the tail vein of the mouse $BDF_1$ (8 week age, male) After feeding for 14 days, the mouse was sacrificed to excise the lungs. The number of colonies of the B16 subline formed on the surface of and in the lungs was counted. The results are shown in Table 3.

TABLE 3

| Drug Added | Concentration | Pulmonary Metastasis (no.) | | | | |
|---|---|---|---|---|---|---|
| | | Mouse 1 | Mouse 2 | Mouse 3 | Mean ± Standard Deviation | % |
| None | | 29 | 32 | 35 | 32 ± 3.0 | 100 |
| N-(3-Phenylpropyl)-1-deoxynojirimycin: | | | | | | |
| | 30 μg/ml | 9 | 22 | 37 | 22.7 ± 14.0 | 68.8 |
| | 100 μg/ml | 4 | 4 | 6 | 4.7 ± 1.2 | 14.7 |
| | 300 μg/ml | 0 | 0 | 3 | 1 ± 1.7 | 3.1 |

As shown in Table 3, N-(3-phenylpropyl)-1-deoxynojirimycin that is the effective ingredient of the present invention shows decrease in the number of colonies formed on the surface of and in the lungs.

TEST EXAMPLE 3

Inhibition of metastasis by N-(3-phenyl-2-propenyl)-1-deoxy-nojirimycin and N-(3-p-chlorophenyl-3-methyl-2-propenyl)-1- deoxynojirimycin:

Inhibition of metastasis was examined in a manner similar to Test Example 2 except that N-(3-phenyl-2-propenyl)-1-deoxy-nojirimycin and N-(3-p-chlorophenyl-3-methyl-2-propenyl)-1-deoxynojirimycin were used instead of N-(3-phenylpropyl)-1-deoxynojirimycin in Test Example 2. In this test example, however, $2.5 \times 10^5$ cells each of the B16 subline were transplanted to 3 mice for each group. The results are shown in Table 4.

TABLE 4

| Drug Added | Concentration | Pulmonary Matastasis (no.) (Mean ± Standard deriation) |
|---|---|---|
| None | | 109 ± 32.0 |
| N-(3-Phenyl-2-propenyl)-1-deoxynojirimycin: | 30 μg/ml | 16.8 ± 12.6 |
| N-(3-p-Chlorophenyl-3-methyl-2 propenyl)-1-deoxynojirimycin: | 30 μg/ml | 14.0 ± 8.9 |

As shown in Table 4, metastasis of the B16 subline of high pulmonary metastasis potential to the lungs was markedly inhibited by N (3-phenyl-2-propenyl)-1-deoxynojirimycin or N-(3-p-chlorophenyl-3-methyl-2-propenyl)-1-deoxynojirimycin.

TEST EXAMPLE 4

Cytotoxic activity of N-(4-phenoxy-trans-2-butenyl)-1-deoxynojirimycin:

The B16 subline of high pulmonary metastatic potential and murine tumor cell line L 929 were cultured in DME medium supplemented with 10% bovine fetal serum at 37° C. in the presence of 5% $CO_2$. Then, cells were detached from the Petri dish with trypsin-EDTA solution. The B16 subline and L 929 were suspended in the medium described above in $1 \times 10^4$ cells/ml and $1 \times 10^3$ cells/ml, respectively. Each suspension, 150 μl, was added to 50 μl of N-(4-phenoxy-trans-2-butenyl)-1-deoxynojirimycin solution or Adriamycin (control) solution. Incubation was performed for 3 days in the B16 subline and for 4 days in L 929. Cell growth was observed with the aid of an inverted microscope to determine the cytotoxicity. The results are shown in Table 5.

TABLE 5

| Drug Added | Concentration | Growth |
|---|---|---|
| Cell Line: B16 subline of High Pulmonary Metastatic Potential | | |
| None | | + |
| N-(4-Phenoxy-trans-2-butenyl)-1-deoxynojirimycin | 3 μg/ml | + |
| | 10 μg/ml | + |
| | 30 μg/ml | + |
| Adriamycin (control) | 0.1 μg/ml | − |
| Cell Line: L 929 | | |
| None | | + |
| N-(4-Phenoxy-trans-2-butenyl)-1-deoxynojirimycin | 3 μg/ml | + |
| | 30 μg/ml | + |
| | 100 μg/ml | + |
| Adriamycin (control) | 1 μg/ml | − |

In the table:
+ indicates growth;
− indicates death.

marked cytotoxicity against the B16 subline of high pulmonary metastatic potential, and L 929 even at a concentration as high as 30 μg/ml.

TEST EXAMPLE 5

Inhibition of metastasis by N-(4-phenoxytrans-2-butenyl)-1-deoxynojirimycin:

The B16 subline of high pulmonary metastatic potential was inoculated into DME medium supplemented with 10% bovine fetal serum and 30 μg/ml of N-(4-phenoxy-trans-2-butenyl)-1-deoxynojirimycin was added thereto followed by incubation at 37° C. for 3 days in the presence of 5% $CO_2$. The cells were detached from the Petri dish with trypsin-EDTA solution. The cells were suspended in PBS- in $1 \times 10^6$ cells/ml as viable cells. This suspension, 0.1 ml, was intravenously injected in the tail vein of the mouse $BDF_1$ (8 week age, male). After feeding for 14 days, the mouse was sacrificed to excise the lungs. The number of colonies of the B16 subline formed on the surface of and in the lung was counted. The results are shown in Table 6.

TABLE 6

| | | Pulmonary Metastasis (no.) | | | | |
|---|---|---|---|---|---|---|
| Drug Added | Concentration | Mouse 1 | Mouse 2 | Mouse 3 | Mean ± Standard Derivation | % |
| None | | 120 | 141 | 145 | 135 ± 13.4 | 100 |
| N-(4-Phenoxy-trans-2-butenyl)-1-deoxy-nojirimycin: | 10 μg/ml | 14 | 48 | 52 | 38 ± 20.9 | 28.1 |

As shown in Table 6. in the test group of N-(4-phenoxy-trans-2-butenyl)-1-deoxynojirimycin that was the effective ingredient of the present invention, the number of colonies on the surface of and in the lungs was decreased.

TEST EXAMPLE 6

Inhibition of metastasis by N-(2-phenoxyethyl)-1-deoxynojirimycin;

Inhibition of metastasis was examined in a manner similar to Test Example 5 except that N-(2-phenoxyethyl)-1-deoxynojirimycin was used instead of N-(4-phenoxy-trans-2-butenyl)-1-deoxynojirimycin in Test Example 5.The results are shown in Table 7.

TABLE 7

| Drug Added | Concentration | Pulmonary Metastasis (no.) (Mean ± Standard Deviation) |
|---|---|---|
| None | | 86 ± 22.1 |
| N-(2-Phenoxyethyl)-1-deoxynojirimycin: | 100 μg/ml | 7 ± 2.1 |

As shown in Table 7, metastasis of the B16 subline of high pulmonary metastatic potential to the lungs was markedly inhibited by N-(2-phenoxyethyl)-1-deoxynojirimycin which was the effective ingredient of the present invention.

TEST EXAMPLE 7

Cytotoxic activity of D-glucaro-δ-lactam calcium salt:

The B16 subline of high pulmonary metastatic potential and murine tumor cell line L 929 were cultured in DME medium supplemented with 10% bovine fetal serum at 37° C. in the presence of 5% $CO_2$. Then, cells were detached from the Petri dish with trypsin-EDTA solution. The B16 subline and L 929 were suspended in the medium described above in $1 \times 10^4$ cells/ml and $1 \times 10^3$ cells/ml, respectively. Each suspension, 150 μl, was added to 50 μl of D-glucaro-δ-lactam calcium salt solution or Adriamycin (control) solutions.

Incubation was performed for 3 days in the B16 subline and for 4 days in L 929. Cell growth was observed with the aid of an inverted microscope to determine the cytotoxicity.

The results are shown in Table 8.

TABLE 8

| Drug Added | Concentration | Growth |
| --- | --- | --- |
| Cell Line: B16 Subline of High Pulmonary Metastatic Potential | | |
| None | | + |
| D-Glucaro-δ-lactam calcium salt | 10 μg/ml | + |
| | 30 μg/ml | + |
| Adriamycin (control) | 0.1 μg/ml | − |
| Cell Line: L 929 | | |
| None | | + |
| D-Glucaro-δ-lactam calcium salt | 10 μg/ml | + |
| | 30 μg/ml | + |
| Adriamycin (control) | 1 μg/ml | − |

In the table:
+ indicates growth;
− indicates death.

As shown in Table 8, D-glucaro-δ-lactam calcium salt which was the effective ingredient of the present invention did not show marked cytotoxicity against the B16 subline and L 929 even at a concentration as high as 30 μg/ml.

TEST EXAMPLE 8

Inhibition of metastasis by of D-glucaro-δ-lactam calcium salt:

The B16 sibline of high pulmonary metastatic potential was inoculated into DME medium supplemented with 10% bovine fetal serum and 10 μg/ml of D-glucaro-δ-lactam calcium salt was added thereto followed by incubation at 37° C. for 3 days in the presence of 5% $CO_2$. The cells were detached from the Petri dish with trypsin-EDTA solution. The cells were suspended in PBS in $1 \times 10^6$ cells/ml as viable cells. This suspension, 0.1 ml, was intravenously injected in the tail vein of the mouse BDF, (8 week age, male). After feeding for 14 days, the mouse was sacrificed to excise the lungs. The number of the colonies formed on the surface of and in the lung was counted. The results are shown in Table 9.

TABLE 9

| | | Pulmonary Metastasis (no.) | | | | |
| --- | --- | --- | --- | --- | --- | --- |
| Drug Added | Concentration | Mouse 1 | Mouse 2 | Mouse 3 | Mean ± Standard Deviation | % |
| None | | 70 | 69 | 68 | 69 ± 1.0 | 100 |
| D-Glucaro-δ-lactam calcium salt | 10 μg/ml | 7 | 4 | 0 | 3.7 ± 3.5 | 5.4 |

As shown in Table 9, metastasis of the B16 subline of high pulmonary, metastatic potential was markedly inhibited by the treatment with D-glucaro-δ-lactam calcium salt that is the effective ingredient of the present invention.

TEST EXAMPLE 9

Inhibition of metastasis by D-glucaro-δ-lactam methyl ester and D-glucaro-δ-lactam ethyl ester:

Inhibition of metastasis was examined in a manner similar to Test Example 8 except that D-glucaro-δ-lactam methyl ester and D-glucaro-δ-lactam ethyl ester were used instead of D-glucaro-δ-lactam calcium salt in Test Example 8. The results are shown in Table 10.

TABLE 10

| Drug Added | Concentration | Pulmonary Metastasis (no.) (Mean ± Standard Deviation) (Mean ± Standard Deviation) |
| --- | --- | --- |
| None | | 82 ± 11.2 |
| D-Glucaro-δ-lactam methyl ester: | 30 μg/ml | 21 ± 8.5 |
| D-Glucaro-δ-lactam ethyl ester: | 30 μg/ml | 13 ± 5.4 |

As shown in Table 10, metastasis of the B16 subline to the lungs was markedly inhibited by D-glucaro-δ-lactam methyl ester or D-glucaro-δ-lactam ethyl ester which were the effective ingredients of the present invention.

TEST EXAMPLE 10

Cytotoxic activity of 2,6-di-O-[1-(p-chlorobenzoyl)-5-methoxy-2-methylindole-3-acetyl]-D-gluco-δ-lactam:

The B16 subline of high pulmonary metastatic potential and murine tumor cell line L 929 were cultured in DME medium supplemented with 10% bovine fetal serum at 37° C. in the presence of 5% $CO_2$. Then, cells were detached from the Petri dish with trypsin-EDTA solution. The B16 subline and L 929 were suspended in the medium described above in $1 \times$ cells/ml and $1 \times 10^3$ cells/ml, respectively. Each suspension, 150 μl, was added to 50 μl of 2,6-di-O-(1-(p-chlorobenzoyl)-5-methoxy-2-methylindole-3-acetyl)-D-gluco-δ-lactam solution or and Adriamycin (control) solutions. Incubation was performed for 3 days in the B16 subline and for 4 days in L 929. Cell growth was observed with the aid of an inverted microscope to determine the cytotoxicity. The results are shown in Table 11.

TABLE 11

| Drug Added | Concentration | Growth |
| --- | --- | --- |
| Cell Line: B16 Subline of High Pulmonary Metastatic Potantial | | |
| None | | + |
| 2,6-Di-O-[1-(p-chloro- | 10 μg/ml | + |

TABLE 11-continued

| Drug Added | Concentration | Growth |
|---|---|---|
| benzoyl)-5-methoxy-2-methylindole-3-acetyl]-D-Gluco-δ-lactam | | |
| Adriamycin (control) | 0.1 μg/ml | — |
| Cell Line: L 929 | | |
| None | | + |
| 2,6-Di-O-[1-(p-chlorobenzoyl)-5-methoxy-2-methylindole-3-acetyl]-D-Gluco- δ-lactam | 3 μg/ml | + |
| | 10 μg/ml | + |
| | 30 μg/ml | + |
| Adriamycin (control) | 1 μg/ml | — |

In the table:
+ indicates growth;
— indicates death.

As shown in Table 11, 2,6-di-O-[1-(p-chlorobenzoyl)-5-methoxy-2-methylindole-3-acetyl]-D-Gluco-δ-lactam which was the effective ingredient of the present invention did not show marked cytotoxity against the B16 subline and L 929 even at a concentration as high as 10 μg/ml.

TEST EXAMPLE 11

Inhibition of metastasis by 2,6-di-O-(acetylsalicyloyl)-D- gluco-δ-lactam:

The B16 subline of high pulmonary metastatic potential was inoculated into DME medium supplemented with 10% bovine fetal serum and 10 μg/ml of 2,6-di-O-(acetylsalicyloyl)-D-gluco-δ-lactam was added thereto followed by incubation at 37° C. for 3 days in the presence of 5% $CO_2$. The cells were detached from the Petri dish with trypsin-EDTA solution. The cells were suspended in PBS- in $1 \times 10^6$ cells/ml as viable cells. This suspension, 0.1 ml, was intravenously injected in the tail vein of the mouse, BDF, (8 week age, male; 1 group, 3 mice). After feeding for 14 days, the mouse was sacrificed to excise the lungs. The number of the colonies of the B16 subline formed on the surface of and in the lungs was counted. The results are shown in Table 12.

TABLE 12

| Drug Added | Concentration | Pulmonary Metastasis (no.) Mean ± Standard Deviation) |
|---|---|---|
| None | | 53 ± 22.4 |
| 2,6-Di-O-(acetylsalicyloyl)-D-gluco-δ-lactam: | 10 μg/ml | 11.2 ± 3.5 |

As shown in Table 12, metastasis of the B16 subline of high pulmonary metastasis potential was markedly inhibited by 2,6-di-O-(acetylsalicyloyl)-D-gluco-δ-lactam which was the effective ingredient of the present invention.

TEST EXAMPLE 12

Cytotoxic activity of 6-0-triphenylmethyl-D-gluco-δ-lactam:

The B16 subline of high pulmonary metastatic potential and murine tumor cell line L 929 were cultured in DME medium supplemented with 10% bovine fetal serum at 37° C. in the presence of 5% $CO_2$. Then, cells were detached from the Petri dish with trypsin-EDTA solution. The B16 subline and L 929 were suspended in the medium described above in $1 \times 10^4$ cells/ml and $1 \times 10^3$ cells/ml, respectively. Each suspension, 150 pi, was added to 50 μl of 6-O-triphenylmethyl-D-gluco-δ-lactam solution or Adriamycin (control) solutions. Incubation was performed for 3 days in the B16 sibline and for 4 days in L 929. Cell growth was observed with the aid of an inverted microscope to determine the cytotoxicity. The results are shown in Table 13.

TABLE 13

| Drug Added | Concentration | Growth |
|---|---|---|
| Cell Line: B16 Subline of High Pulmonary Metastatic Potential | | |
| None | | + |
| 6-O-Triphenylmethyl-D-Gluco-δ-lactam | 3 μg/ml | + |
| | 10 μg/ml | + |
| | 30 μg/ml | + |
| Adriamycin (control) | 0.1 μg/ml | — |
| Cell Line: L 929 | | |
| None | | + |
| 6-O-Triphenylmethyl-D-Gluco-δ-lactam | 10 μg/ml | + |
| | 30 μg/ml | + |
| Adriamycin (control) | 1 μg/ml | — |

In the table:
+ indicates growth;
— indicates death.

As shown in Table 13, 6-O-triphenylmethyl-D-gluco-δ-lactam which was the effective ingredient of the present invention did not show marked cytotoxicity against the B16 subline and L 929 even at a concentration as high as 30 μg/ml.

TEST EXAMPLE 13

Inhibition of metastasis by 6-O-triphenylmethyl-D-gluco-δ-lactam:

The B16 subline of high pulmonary metastatic potential was inoculated into DME medium supplemented with 10% bovine fetal serum and 30 μg/ml of 6-O-triphenylmethyl-D-gluco-δ-lactam was added thereto followed by incubation at 37° C. for 3 days in the presence of 5% $CO_2$. The cells were detached from the Petri dish with trypsin-EDTA solution. The cells were suspended in PBS- in $1 \times 10^6$ cells/ml as viable cells. This suspension, 0.1 ml, was intravenously injected in the tail vein of the mouse $BDF_1$ (8 week age, male; 1 group, 3 mice). After feeding for 14 days, the mouse was sacrificed to excise the lungs. The number of colonies of the B16 subline on the surface of and in the lungs was counted. The results are shown in Table 14.

TABLE 14

| Drug Added | Concentration | Pulmonary Metastasis (no.) (Mean ± Standard Deviation) |
|---|---|---|
| None | | 92 ± 21.3 |
| 6-O-Triphenylmethyl-D-gluco-δ-lactam | 30 μg/ml | 17 ± 8.5 |

As shown in Table 14, metastasis of the B16 subline to the lungs was markedly inhibited by 6-O-triphenylmethyl-D-gluco-δ-lactam which was the effective ingredient of the present invention.

TEST EXAMPLE 14

Inhibition of metastasis by 1-deoxynojirimycin:

The B16 subline of high pulmonary metastatic potential was inoculated into DME medium supplemented with 10% bovine fetal serum and 30 μg/ml of 1-deoxynojirimycin was added thereto followed by incubation at 37° C. for 3 days in the presence of 5% $CO_2$. In this case, cytotoxicity by this substance was hardly observed. Next, the cells were detached from the Petri dish with trypsin-EDTA solution. The cells were suspended in PBS- in $1 \times 10^6$ cells/ml as viable cells. This suspension, 0.1 ml, was intravenously injected in the tail vein of the mouse $BDF_1$ (8 week age, male; 1 group, 3 mice). After feeding for 14 days,, the mouse was sacrificed to excise the lungs. The number of colonies of the B16 subline on the surface of and in the lungs was counted. The results are shown in Table 15.

TABLE 15

| Drug Added | Pulmonary Metastasis (no.) (Mean ± Standard Deviation) |
|---|---|
| None | 119 ± 37 |
| 1-Deoxynojirimycin (30 μg/ml) | 31 ± 11 |

As shown in Table 15, the number of colonies on the surface of and in the lungs was markedly inhibited by treatment with 1-deoxynojirimycin which was the effective ingredient of the present invention.

While the invention has been described in detail and with reference to specific embodiments thereof, it will be apparent to one skilled in the art that various changes and modifications can be made therein without departing from the spirit and scope thereof.

What is claimed is:

1. A method of inhibiting cancer cell metastasis comprising administering to a host afflicted with cancer cells a pharmaceutical preparation comprising as an active ingredient an effective amount of a compound represented by the formula (I):

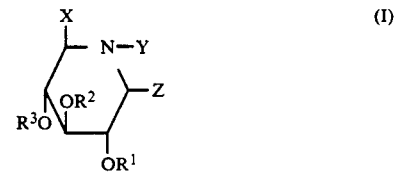

wherein
X is —CH$_2$OH;
Y is a hydrogen atom;
Z is a hydrogen atom; and
R$^1$, R$^2$ and R$^3$ and each a hydrogen atom, and a pharmaceutically acceptable carrier therefor.

* * * * *